United States Patent
Kovi et al.

(10) Patent No.: US 8,450,487 B2
(45) Date of Patent: May 28, 2013

(54) PROCESS FOR THE PREPARATION OF CIS-2-METHYLSPIRO (1,3-OXATHIOLANE 5-3') QUINUCLIDINE

(75) Inventors: Ravishanker Kovi, Monroe, NJ (US); Jayaraman Kannapan, Gujarat (IN); Talluri Buhshaiah Chowdari, Andhra Pradesh (IN); Chirag Vasantlal Shah, Gujarat (IN)

(73) Assignee: Apicore, LLC, Somerset, NJ (US)

( * ) Notice: Subject to any disclaimer, the term of this patent is extended or adjusted under 35 U.S.C. 154(b) by 132 days.

(21) Appl. No.: 12/796,308

(22) Filed: Jun. 8, 2010

(65) Prior Publication Data

US 2011/0301352 A1 Dec. 8, 2011

(51) Int. Cl.
*C07D 453/00* (2006.01)

(52) U.S. Cl.
USPC ........................................................ 546/18

(58) Field of Classification Search
None
See application file for complete search history.

(56) References Cited

U.S. PATENT DOCUMENTS

| | | | |
|---|---|---|---|
| 4,855,290 A | 8/1989 | Fisher et al. |
| 4,861,886 A | 8/1989 | Haga et al. |
| 4,981,858 A | 1/1991 | Fisher et al. |
| 5,407,938 A | 4/1995 | Fisher et al. |
| 5,571,918 A | 11/1996 | Hayashi et al. |
| 5,580,880 A | 12/1996 | Handa et al. |
| 2008/0249312 A1 | 10/2008 | Bratovanov et al. |

OTHER PUBLICATIONS

International Search Report and Written Opinion for corresponding PCT Application No. PCT/US11/36631, Aug. 12, 2011 (ISA/210 and ISA/237).
International Preliminary Report on Patentability for corresponding PCT Application No. PCT/US11/36631, Dec. 20, 2012.

*Primary Examiner* — Janet Andres
*Assistant Examiner* — Timoth R. Rozof
(74) *Attorney, Agent, or Firm* — Timothy X. Gibson, Esq.; Gibson & Dernier LLP

(57) ABSTRACT

Methods are provided for making pharmaceutical-grade cis-2-methylspiro(1,3-oxathiolane-5,3')quinuclidine and pharmaceutically acceptable salts thereof by isomerizing racemic 2-methylspiro(1,3-oxathiolane-5,3')quinuclidine to cis-2-methylspiro(1,3-oxathiolane-5,3')quinuclidine and subsequent purification of the C-MSOQ by salt formation with inexpensive and commercially available material such as sulfuric acid. Purification methods are disclosed which employ an organic solvent/water system and recrystallization with an organic solvent such as acetone.

15 Claims, No Drawings

PROCESS FOR THE PREPARATION OF CIS-2-METHYLSPIRO (1,3-OXATHIOLANE 5-3') QUINUCLIDINE

FIELD OF INVENTION

The present invention relates to improved, industrially acceptable processes for the preparation of pharmaceutical grade cis-2-methylspiro(1,3-oxathiolane-5,3')quinuclidine.

BACKGROUND OF INVENTION

Cis-2-methylspiro(1,3-oxathiolane-5,3')quinuclidine (C-MSOQ), also known as cevimeline, is a pharmaceutical compound useful for the treatment of diseases of the central nervous system in mammals, particularly for the treatment of diseases due to disturbances of central cholinergic function and autoimmune disease such as Sjögren's syndrome.

U.S. Pat. No. 4,855,290 describes a process of making the intermediate 3-hydroxy-3-mercaptomethylene quinuclidine using a sodium hydroxide/dichloromethane system and hydrogen sulfide at 40° C. with 33 to 40% yield. Drawbacks of this process include providing the intermediate in very low yields due to the decomposition of the intermediate in the given reaction conditions, side product "diol" formation due to the susceptibility of the epoxide moiety to form diol with the sodium hydroxide solution at the recommended temperature, and the requirement of a continuous stream of hydrogen sulfide gas.

U.S. Pat. No. 5,571,918 describes the preparation of the intermediate 3-hydroxy-3-mercaptomethylene quinuclidine by a process of passing hydrogen sulfide gas continuously with a special type of catalyst, p-toluene sulfonic anhydride. Drawbacks of this process include an excess use of hydrogen sulfide gas by passing the hydrogen sulfide gas continuously for more than 6 hours and the requirement of an additional catalyst to complete the reaction. The amount of hydrogen sulfide used for the process is quite high—18 grams/per minute flow for 6 hours, therefore for a 13.9 gm batch of product the required quantity of hydrogen sulfide gas is 6.5 kg.

U.S. Published Patent Application No. 2008/0249312 describes a two way process of making the aforementioned intermediate using thiol-acetic acid, an industrially toxic chemical with a highly unpleasant odor, with a yield of approximately 60 to 70%. This process requires first making the salt and then isolating the salt to obtain the salt of the intermediate, which is then used for the subsequent reaction.

For the preparation of the cis isomer of cevimeline, U.S. Pat. No. 4,855,290 describes a process employing multiple recrystallization of the racemic 2-methylspiro(1,3-oxathiolane-5,3')quinuclidine. Drawbacks of this process include lack of scalability due to multiple recrystallization steps and the requirement of enrichment of the cis-isomer from mother liquor involving chromatographic purification and isolation. In addition to unsuitability for commercialization, the resultant yield after several steps of purification is less than 10%.

U.S. Pat. No. 4,981,858 involves a resolution of enantiomers of cis and trans isomers of 2-methylspiro(1,3-oxathiolane-5,3')quinuclidine individually by a tartaric acid resolution technique. There is no discussion regarding preparation and purification of the cis isomer from a racemic 2-methylspiro(1,3-oxathiolane-5,3')quinuclidine.

U.S. Pat. No. 4,861,886 describes the conversion of pure trans 2-methylspiro(1,3-oxathiolane-5,3')quinuclidine to the cis isomer under different conditions. However, no method is taught or disclosed for complete conversion of the trans isomer to the cis isomer. None of the techniques describe how to obtain pharmaceutical quality cis-2-methylspiro(1,3-oxathiolane-5,3')quinuclidine.

U.S. Pat. No. 5,571,918 describes the conversion of racemic 2-methylspiro(1,3-oxathiolane-5,3')quinuclidine to the cis isomer using stannic chloride as a catalyst. There is no teaching of any process or technique to obtain the cis isomer with greater than 98.5% purity when analyzed by HPLC.

Therefore, there is a need for an industrially viable process that achieves better yields of cis-form-2-methylspiro(1,3-oxathiolane-5,3')quinuclidine and employs less expensive reagents and solvents, resulting in lower production costs. Furthermore, there is further a need for a process which can generate cis-form-2-methylspiro(1,3-oxathiolane-5,3')quinuclidine of a pharmaceutically acceptable isomeric purity, i.e., at least 99.0% purity or greater, without the need for multiple tedious isolation, purification and/or separation steps.

SUMMARY OF THE INVENTION

Industrially advantageous methods are provided for making pharmaceutical grade cis-2-methylspiro(1,3-oxathiolane-5,3')quinuclidine (sometimes referred to herein as C-MSOQ) and pharmaceutically acceptable salts thereof. The disclosed methods provide surprisingly high yields and purity of C-MSOQ, cevimeline hydrochloride and hydrate forms thereof through the control of intermediates using novel solvent systems and reactions.

In one embodiment the disclosed method provides cis-2-methylspiro(1,3-oxathiolane-5,3')quinuclidine by isomerizing racemic 2-methylspiro(1,3-oxathiolane-5,3')quinuclidine to cis-2-methylspiro(1,3-oxathiolane-5,3')quinuclidine and subsequent purification of the C-MSOQ by salt formation with inexpensive and commercially available material such as sulfuric acid. This salt is purified by a novel purification method which employs an organic solvent/water system and recrystallization with an organic solvent such as acetone.

In one embodiment, the method involves preparing 3-hydroxy-3-methyl-quinuclidine, isomerizing racemic 2-methylspiro(1,3-oxathiolane-5,3')quinuclidine (65:35 trans:cis isomer) to initially about 90% cis isomer with a Lewis acid such as titanium tetrachloride and subsequent purification by acid addition salt formation with an inorganic acid such as sulfuric acid. The resulting sulfate salt is further purified with an organic solvent/water acetone medium to produce pharmaceutical-grade cis-2-methylspiro(1,3-oxathiolane-5,3') quinuclidine wherein the cis isomer purity is greater than or equal to 99.5% by HPLC.

In another embodiment, a novel simple, single-step method is disclosed in which the intermediate 3-hydroxy-3-mercaptomethylene quinuclidine is prepared from the epoxide of 3-methylene quinuclidine using hydrogen sulfide in molar quantity in a solvent medium of methanol. This method is industrially more acceptable and inexpensive, and achieves much higher yields, compared to prior art processes referenced above. Employing hydrogen sulfide in a molar ratio avoids any excess quantity of hydrogen sulfide. The disclosed processes do not require any catalyst. The reaction time is much shorter than prior art processes, which helps greatly to stabilize the 3-hydroxy-3-mercapto methyl quinuclidine—and reduces plant utilization time and equipment usage.

In one embodiment, in situ reaction of the 3-hydroxy-3-mercaptomethyl quinuclidine with acetaldehyde and boron trifluoride etherate is employed to obtain racemic 2-methylspiro(1,3-oxathiolane-5,3')quinuclidine. The racemic 2-methylspiro(1,3-oxathiolane-5,3')quinuclidine is isomerized to cis-2-methylspiro(1,3-oxathiolane 5,3')quinuclidine using titanium tetrachloride and further purified by salt formation and recrystallisation with concentrated sulfuric acid and an organic solvent to obtain pharmaceutically acceptable quality cis-2-methylspiro(1,3-oxathiolane 5,3')quinuclidine of >99.5% purity by HPLC.

These and other aspects of the invention will be apparent to those skilled in the art.

DETAILED DESCRIPTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

In accordance with one embodiment a method is disclosed for the preparation of the key intermediate 3-hydroxy-3-mercaptomethyl quinuclidine by passing a fixed quantity of hydrogen sulfide gas to the epoxide of 3-methylene quinuclidine in a novel solvent medium of methanol.

Scheme 1 below shows a method of preparing the epoxide of 3-methylene quinuclidine, which method is known in the art.

SCHEME I

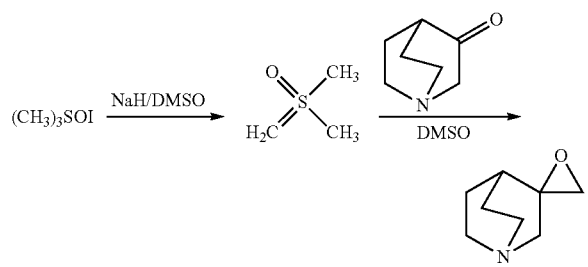

As shown in Scheme II below, the epoxide of 3-methylene quinuclidine is dissolved in a medium of dichloromethane/methanol and a fixed quantity of hydrogen sulfide is introduced to the solution for a period of 1 to 3 hours at a temperature range of −10 to 5° C. The gas flow is stopped and the reaction mixture is stirred for another 1 to 3 hours to convert 3-methylene quinuclidine to 3-hydroxy-3-methyl quinuclidine. In a preferred embodiment, as shown in Stage I of Scheme II, the amount of hydrogen sulfide used is either exactly what is required or slightly in excess of the mole ratio, to avoid excessive usage of this toxic gas. Excess hydrogen sulfide may be removed by passing nitrogen gas through the reaction mixture.

As shown in Stage II below, the resulting thiol derivative is converted in situ to 2-methylspiro(1,3-oxathiolane-5,3')quinuclidine. The disclosed one-pot conversion of the epoxide of 3-hydroxy-3-mercaptomethyl quinuclidine to 2-methylspiro (1,3-oxathiolane-5,3')quinuclidine is simple, achieves high yields and is easily scalable, all with inexpensive reagents/chemicals in a short reaction time. Surprisingly, it was found that methanol can be used as a good solvent medium for this reaction. This finding is contrary to the usage of methanol for these type of reactions, as it is well known methanol can compete as a nucleopile with hydrogen sulfide.

The compound 3-hydroxy-3-mercaptomethylquinuclidine is very unstable. The disclosed methods of preparation allow for the next step without any serious difficulties and result in very high yield of 2-methylspiro(1,3-oxathiolane 5,3')quinuclidine. Two-way addition of 3-hydroxy 3-methylquinuclidine and boron trifluoride to an acetaldehyde solution at low temperature minimizes impurity formation and maximizes the yield.

SCHEME II

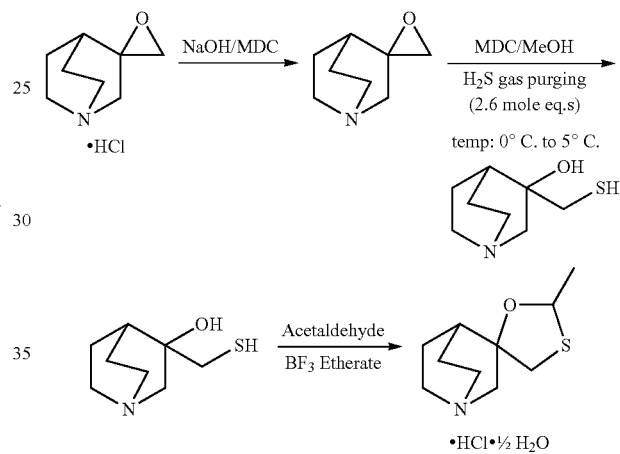

Stage I of Scheme III shown below involves the isomerization of the racemic 2-methylspiro(1,3-oxathiolane-5,3')quinuclidine. Stage II illustrates the purification process to obtain the cis isomer with >99.5% purity by HPLC.

In a preferred embodiment a mixture of racemic 2-methylspiro(1,3-oxathiolane-5,3')quinuclidine with an isomer ratio of about 65:35 cis:trans respectively is isomerized initially to 90% cis 2-methylspiro(1,3-oxathiolane-5,3')quinuclidine with the Lewis acid catalyst titanium tetrachloride in an organic solvent such as acetone, dichlororomethane, dimethyl sulfoxide, methyl isobutyl ketone or a mixture thereof. A suitable quantity of titanium tetrachloride preferably, 0.5 to 5 moles, is added to the racemic 2-methylspiro(1,3-oxathiolane-5,3')quinuclidine in a solvent system as described above. The reaction mixture is stirred for 1 to 48 hours at a temperature range of −5 to 50° C. After the completion of the isomerization, the reaction mass is worked up to generate the free base of cis-2-methylspiro(1,3-oxathiolane-5,3')quinuclidine having nearly 90% purity of cis isomer by HPLC.

The above-generated cis isomer is further converted to greater than or equal to 99.5% cis isomer (HPLC purity) by salt formation with sulfuric acid, purification and finally to hydrochloride salt. A suitable amount of sulfuric acid, preferably 1.0 to 3.0 equivalents relative to the input quantity, is added to the above-described nearly 90% pure cis 2-methylspiro(1,3-oxathiolane-5,3')quinuclidine base at a temperature range of 0 to 30° C. After addition, the reaction mass is stirred for 2 to 24 hours at a temperature range of 0 to 115° C., preferably 20 to 40° C., and filtered to isolate the sulfate salt. The above prepared salt can be recrystallized in a solvent such as acetone, ethyl methyl ketone, methyl isobutyl ketone or a mixture thereof at different temperature ranges to obtain the desired pharmaceutically acceptable grade cis-2-methylspiro (1,3-oxathiolane-5,3')quinuclidine having a purity of 99.5% of cis-isomer by HPLC.

SCHEME-III

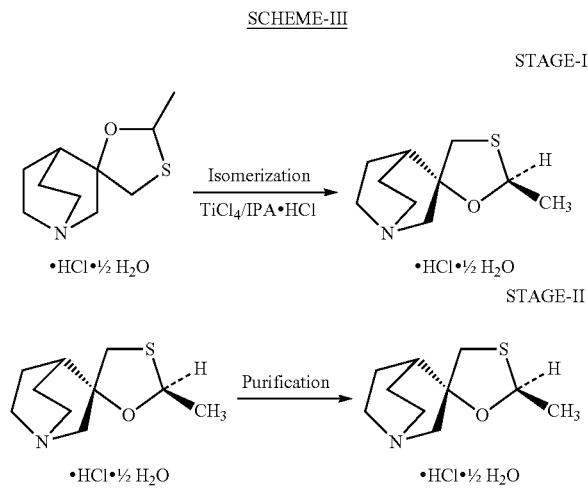

EXAMPLES

Example I

Preparation of 3-hydroxy 3-mercapto methylquinuclidine

A solution of the epoxide of 3-methylene quinuclidine (100 g, 0.719 moles) in dichloromethane was cooled to a temperature between about 0 to 5° C. The solution was charged with methanol (100 ml). The mass was stirred for 10 to 15 minutes at this temperature range. To this cold solution hydrogen sulfide gas (50 g, 1.4 mol) was passed and after the passing was complete, the reaction was continued at this temperature for 2 to 3 hours, monitored by gas chromatography, whereupon the peak of epoxide of 3-methylene quinuclidine disappeared. After completion of the reaction, a dichloromethane solution of 3-hydroxy 3-mecapto methylquinuclidine in methanol was obtained. This solution was used for the next step.

Example II

A solution of acetaldehyde (250 ml) in dichloromethane (1000 ml) was cooled to 0 to 5° C. To this solution was charged the 3-hydroxy-3-mecapto methylquinuclidine solution (100 g epoxide equivalent) prepared in Example I. Boron trifluoride etherate (320 ml) was added simultaneously drop wise over 2 to 3 hours. After completion of the addition, the reaction mass was stirred at 20 to 25° C. for an additional 3 hours. The reaction mass was cooled to 0 to 5° C. A solution of sodium hydroxide (150 g dissolved in 150 ml water) was charged to the solution and the pH of the mixture was adjusted to 12 to 14. The layers were separated. The dichloromethane layer was washed with 5% sulfuric acid solution (500 ml). The product was extracted again in di-isoproyl ether with basification of the aqueous layer to pH 10 to 12. The organic layer containing the product was separated and the base converted to a hydrochloride salt by acidification with IPA/HCl solution to yield 65 g of the racemic cevimeline hydrochloride with 65:35 ratio of cis:trans isomer by HPLC.

Example III

Dichloromethane (200 ml) was charged in a vessel. To this was charged (10.0 g) of racemic mixture of cis/trans cevimeline having a 65:35 ratio of cis:trans isomer. The reaction mass was stirred for 10 to 15 minutes at 20 to 25° C. 1.0 ml of IPA was charged to the reaction mass. The reaction mass was cooled to −5 to 0° C. Anhydrous titanium tetrachloride (7.0 ml) was charged to the reaction mass over 5 to 10 minutes. After addition, stirring was continued for 18 to 24 hours at 20 to 30° C. After completion of the reaction, the reaction mass was cooled to 0 to 5° C. Process water (100 ml) was added and the mass was stirred for 10 to 15 minutes. The layers were separated. The dichloromethane layer was washed with 5% sulfuric acid (2×50 ml) and the layers separated. To the combined aqueous layer, di-isopropyl ether (100 ml) was charged and the pH of the solution adjusted 10 to 12. The layers were separated and the aqueous portion re-extracted with di-isopropyl ether (50 ml). The combined organic layer was dried with anhydrous sodium sulfate. To the dried solution was charged IPA/HCl solution to acidic. The separated solid was stirred and filtered at 0 to 5° C. for 30 to 45 minutes. The solid was washed with chilled di-isopropyl ether (2×10 ml). The solid was suction dried at 50 to 60° C. under vacuum to yield 6.5 g of the product with cis isomer of cevimeline hydrochloride >90% purity by HPLC.

Example IV

Dichloromethane (200 ml) was charged to a vessel and to this was added (10.0 g) of racemic mixture of cis/trans cevimeline with a ratio of about 65:35 cis:trans isomer as prepared in Example III. The reaction mass was stirred for 10 to 15 minutes at 20 to 25° C. 1.0 ml IPA was charged to the vessel and the reaction mass cooled to −5 to 0° C. 1.0 ml DMSO was charged to the mass. Anhydrous titanium tetrachloride (7.5 ml) was added drop wise over 5 to 10 minutes. After this addition, stirring was continued for 6 hours at 20 to 30° C. The reaction mass was then cooled and processed as in Example III to yield 6.0 g of the product of cis isomer of cevimeline hydrochloride with >90% purity by HPLC.

Example V

Charged chloroform (35 ml) to a vessel and to this charged (5.0 g) of a racemic mixture of cis/trans cevimeline with about 65:35 ratio of cis:trans isomer. Stirred the reaction mass for 10 to 15 minutes at 20 to 25° C. Cooled the reaction mass to −5 to 0° C. Charged anhydrous titanium tetrachloride (3.5 ml) drop wise over 10 to 15 minutes. After addition, continued stirring for 24 hours at 20 to 30° C. The reaction mass was then cooled and processed as in Example III to yield 3.0 g of the product of cis isomer of cevimeline hydrochloride with >90% purity by HPLC.

Example VI

Charged di-isopropyl ether (DIPE) (100 ml) in a vessel and to this charged cevimeline hydrochloride (10.0 g with cis isomer>90% purity and prepared by any one of the above methods). Cooled to 0 to 10° C. Charged concentrated sodium hydroxide solution drop wise to adjust the solution to pH above 12 (pH around 12 to 14). Stirred for 15 to 20 minutes and separated the DIPE layer. Reextracted the aqueous layer with DIPE and distilled off the organic layer, leaving a thick residue. To this residue, charged acetone (10 ml) and continued the distillation to remove the traces of DIPE. Charged acetone (100 ml) to the residue and stirred for 10 to 15 minutes. Cooled the solution to 0 to 5° C. Charged concentrated sulfuric acid (2.5 ml) slowly at the above temperature range. Stirred the separated solid for 30 minutes at 0 to 5° C. Raised the reaction mass temperature to 55 to 60° C. Stirred for 2 hrs and then cooled to 0 to 10° C. Stirred for 30 minutes. Filtered the solid and washed it with chilled acetone (10 ml). Suction dried the solid well and dried the solid at 50 to 60° C. to obtain 9.0 g of the product of cis isomer of cevimeline sulfate with >97% purity HPLC.

Charged cevimeline sulfate to a solution of di-isopropyl ether (100 ml) and cooled the solution to 0 to 10° C. Charged concentrated sodium hydroxide solution drop wise to adjust the pH of the solution to above 12. Stirred for 15 to 20 minutes and separated the DIPE layer. Re-extracted the aqueous layer with DIPE and dried the total DIPE layer with anhydrous sodium sulfate. Cooled the dried DIPE layer to 0 to 10° C. and charged IPA/HCl solution to acidic. Stirred the separated solid at this temperature for 30 to 45 minutes. Filtered the solid and washed it with chilled DIPE (10.0 ml). Suction dried the solid well and dried the solid at 50 to 60° C. to obtain 6.0 g of the cevimeline hydrochloride with cis isomer >97% by HPLC.

Example VII

Charged DIPE (60 ml) to a vessel and to this charged cevimeline hydrochloride (prepared from Example VI) (6.0 g with 97% cis isomer). Cooled the solution to 0 to 10° C. Charged concentrated sodium hydroxide solution drop wise to adjust pH of the solution to above 12. Stirred for 15 to 20 minutes and separated the DIPE layer. Re-extracted the aqueous layer with DIPE and distilled off the organic layer, leaving a thick residue. To this residue, charged acetone (6.0 ml) and continued the distillation to remove traces of DIPE. Charged acetone (60 ml) to the residue and stirred for 10 to 15 minutes. Cooled the solution to 0 to 5° C. Charged sulfuric acid (3.0 ml) slowly at the above temperature range. Raised the reaction mass temperature to 55 to 60° C. Charged sulfuric acid (0.6 ml). Stirred for 2 hrs and then cooled to 0 to 10° C. Stirred for 30 minutes. Filtered the solid and washed it with chilled acetone (10 ml). Suction dried the solid well and dried the solid at 50 to 60° C. to obtain 6.0 g of the product as cevimeline sulfate with cis isomer purity >99.5% by HPLC.

Charged DIPE (60 ml) to a vessel and to this charged the above cevimeline sulfate (99.5% cis isomer). Cooled the solution to 0 to 10° C. Charged concentrated sodium hydroxide solution drop wise to adjust the pH of the solution to above 12. Stirred for 15 to 20 minutes and separated the DIPE layer. Re-extracted the aqueous layer with DIPE and dried the total DIPE layer with anhydrous sodium sulfate. Cooled the dried DIPE layer to 0 to 10° C. and charged IPA/HCl solution to acidic. Stirred the separated solid at this temp for 30 to 45 minutes. Filtered the solid and washed it with chilled DIPE (9.0 ml). Suction dried the solid well and dried the solid at 50 to 60° C. to obtain 3.6 g of the cevimeline hydrochloride with cis isomer >99.5% with individual impurities below 0.10% by HPLC.

Example VIII

Charged ethyl methyl ketone (40 ml) to a vessel and to this charged cevimeline free base with cis isomer >90% by HPLC (4.0 g) (prepared by any one of the above methods given in Examples III to V). Stirred for 10 to 15 minutes to obtain a clear solution. Cooled the solution to 0 to 5° C. Charged concentrated sulfuric acid (1.3 ml) drop wise over 30 minutes and stirred the resultant liberated sulfate salt for 30 minutes at 0 to 5° C. Then slowly raised the temperature to reflux temperature and continued the reflux for 60 to 90 minutes. The reaction mass was then cooled and processed as in Example VI to yield 4.0 g of the product cevimeline sulfate with cis isomer >97% purity by HPLC.

Charged DIPE (260 ml) to a vessel and to this charged the above cevimeline sulfate (4.0 g with 97% cis isomer). Cooled the solution to 0 to 10° C. and proceeded as in Example VI to obtain 2.5 g of cevimeline hydrochloride with cis isomer >97% purity by HPLC.

Example IX

Charged DIPE (26 ml) to a vessel and to this charged cevimeline hydrochloride (2.6 g with 97% cis isomer as prepared in Example VIII). Cooled the solution to 0 to 10° C. Charged concentrated sodium hydroxide solution drop wise to adjust pH of the solution to above 12. Stirred for 15 to 20 minutes and separated the DIPE layer. Re-extracted the aqueous layer with DIPE and distilled off the organic layer, leaving a thick residue. To this residue, charged acetone (6.0 ml) and continued the distillation to remove traces of DIPE. Charged acetone (60 ml) to the residue and stirred for 10 to 15 minutes. Cooled the solution to 0 to 5° C. Charged sulfuric acid (1.3 ml) slowly at the above temperature range. Raised the reaction mass temperature to 55 to 60° C. Charged sulfuric acid (0.26 ml) and proceeded as in Example VII to yield 2.6 g of cevimeline sulfate with >99.5% cis isomer by HPLC.

Charged DIPE (60 ml) to a vessel and to this charged the above cevimeline sulfate (2.6 g, 99.5% cis isomer). Cooled the solution to 0 to 10° C. and proceeded as in Example VII to yield 1.7 g of the cevimeline hydrochloride with cis isomer >99.5% with individual impurities below 0.10% by HPLC.

Example X

Charged methyl isobutyl ketone (60 ml) and to this charged cevimeline free base with cis isomer >90% by HPLC (5.0 g) (prepared by any one of the above methods given in Examples III to V). Stirred for 10 to 15 minutes to obtain a clear solution. Cooled the solution to 0 to 5° C. Charged concentrated sulfuric acid (1.6 ml) drop wise over 30 minutes and stirred the resultant liberated sulfate salt for 30 minutes at 0 to 5° C. Then slowly raised the temperature to reflux temperature and continued the reflux for 60 to 90 minutes. The reaction mass was then cooled and processed as in Example VI to yield 3.0 g of the cevimeline sulfate with cis isomer >97% purity by HPLC.

Charged DIPE (26 ml) to a vessel and to this charged the above cevimeline sulfate (3.0 g with 97% cis isomer). Cooled the solution to 0 to 10° C. and proceeded as in Example VI to obtain 2.0 g of cevimeline hydrochloride with cis isomer >97% purity by HPLC.

Example XI

Charged DIPE (20 ml) to a vessel and to this charged cevimeline hydrochloride prepared from Example X (2.0 g with 97% cis isomer). Cooled the solution to 0 to 10° C. Charged concentrated sodium hydroxide solution drop wise to adjust pH of the solution to above 12. Stirred for 15 to 20 minutes and separated the DIPE layer. Re-extracted the aqueous layer with DIPE and distilled off the organic layer, leaving a thick residue. To this residue, charged acetone (2.0 ml) and continued the distillation to remove traces of DIPE. Charged acetone (20 ml) to the residue and stirred for 10 to 15 minutes. Cooled the solution to 0 to 5° C. Charged sulfuric acid (1.0 ml) slowly at the above temperature range and raised the reaction mass temperature to 55 to 60° C. Charge sulfuric acid (0.2 ml) and proceeded as in Example VII to yield 2.0 g of cevimeline sulfate with >99.5% cis isomer by HPLC.

Charged DIPE (20 ml) to a vessel and to this charged the above cevimeline sulfate (99.5% cis isomer). Cooled the solution to 0 to 10° C. and proceeded as in Example VII to yield 1.7 g of the cevimeline hydrochloride with cis isomer >99.5% with individual impurities below 0.10% by HPLC.

Example XII

Charged toluene (50 ml) and to this charged cevimeline free base with cis isomer >90% (5.0 g) (prepared by any one of the above methods given in examples III to V). Stirred for 10 to 15 minutes to obtain a clear solution. Cooled the solution to 0 to 5° C. Charged concentrated sulfuric acid (1.3 ml) drop wise over 30 minutes and stir the resultant liberated sulfate salt for 30 minutes at 0 to 5° C. Then slowly raised the temperature to reflux temperature (100 to 115° C.) and continued the reflux for 60 to 90 minutes. The reaction mass was then cooled and processed as in Example VI to yield 3.5 g of cevimeline sulfate with cis isomer >97% purity by HPLC.

Charged DIPE (35 ml) to a vessel and to this charged the above cevimeline sulfate (3.5 g with 97% cis isomer). Cooled the solution to 0 to 10° C. and proceeded as in Example VI to obtain 2.0 g of cevimeline hydrochloride with cis isomer >97% purity by HPLC.

Charged DIPE (20 ml) to a vessel and to this charged cevimeline hydrochloride (prepared from Example XII) (2.0 g with 97% cis isomer). Cooled the solution to 0 to 10° C. Charged concentrated sodium hydroxide solution drop wise to adjust pH of the solution to above 12. Stirred for 15 to 20 minutes and separated the DIPE layer. Re-extracted the aqueous layer with DIPE and distilled off the organic layer, leaving a thick residue. To this residue, charged acetone (2.0 ml) and continued the distillation to remove traces of DIPE. Charged acetone (20 ml) to the residue and stirred for 10 to 15 minutes. Cooled the solution to 0 to 5° C. Charged sulfuric acid (1.0 ml) slowly at the above temperature range and raised the reaction mass temperature to 55 to 60° C. Charged sulfuric acid (0.2 ml) and proceeded as in Example VII to yield 2.0 g of cevimeline sulfate with >99.5% cis isomer by HPLC.

Charged DIPE (20 ml) to a vessel and to this charged the above cevimeline sulfate (99.5% cis isomer). Cooled the solution to 0 to 10° C. and proceeded as in Example VII to yield 1.8 g of the cevimeline hydrochloride with cis isomer >99.5% with individual impurities below 0.10% by HPLC.

While the preferred embodiments have been described and illustrated it will be understood that changes in details and obvious undisclosed variations might be made without departing from the spirit and principle of the invention and therefore the scope of the invention is not to be construed as limited to the preferred embodiment.

What is claimed is:

1. A process for the preparation of pharmaceutical grade cis-2-methylspiro(1,3-oxathiolane-5,3')quinuclidine hydrochloride having a purity >99.5% comprising:

a) treating an epoxide of 3-methylenequinuclidine with hydrogen sulfide gas in a solvent selected from the group consisting of methanol, isopropanol, butanol, and mixtures thereof to obtain 3-hydroxy-3-mercaptomethyl quinuclidine;
    b) treating 3-hydroxy-3-mercaptomethyl quinuclidine with acetaldehyde in the presence of a boron trifluoride etherate to generate 2-methylspiro(1,3-oxathiolane-5,3')quinuclidine base;
    c) treating the 2-methylspiro(1,3-oxathiolane-5,3')quinuclidine base with hydrochloric acid to form a racemic hydrochloride salt;
    d) isomerizing the racemic hydrochloride salt with a Lewis acid and an organic solvent to obtain the isomer cis-2-methylspiro(1,3-oxathiolane-5,3')quinuclidine having a purity of >90%;
    e) Purifying the cis isomer having >90% purity by treatment with an inorganic acid and an organic solvent to obtain the cis isomer having a purity of >99.5%.

2. The process according to claim 1 wherein the quantity of hydrogen sulfide gas employed is from 1 to 5 moles.

3. The process according to claim 1 wherein the step of treating an epoxide of 3-methylenequinuclidine, the solvent is methanol.

4. The process according to claim 1 wherein excess hydrogen sulfide is removed by passing nitrogen gas through the reaction mixture.

5. The process according to claim 1 wherein the preparation of 3-hydroxy-3-mercaptomethyl quinuclidine is carried out at a temperature range of −10 to 5° C.

6. The process according to claim 1 wherein the prepared 3-hydroxy 3-mercaptomethyl quinuclidine is not isolated and carried in situ to next step.

7. The process according to claim 1 wherein the formation of 2-methylspiro(1,3-oxathiolane5,3') quinuclidine base from 3-hydroxy-3-mercaptomethyl quinuclidine is carried out at 0 to 30° C. in the presence of 1 to 5 mole of a catalyst per mole of 3-hydroxy-3-mercaptomethyl quinuclidine.

8. The process according to claim 1 wherein the Lewis acid in the isomerizing step is titanium tetrachloride.

9. The process according to claim 8 wherein the quantity of titanium tetrachloride employed is from 1 to 10 moles.

10. The process according to claim 1 wherein the solvent used for the isomerizing step is selected from the group consisting of dichloromethane, methanol, dimethyl sulfoxide, toluene and mixtures thereof.

11. The process according to claim 1 wherein the isomerizing step is carried out at a temperature of −10 to 50° C.

12. The process according to claim 1 wherein the inorganic acid used in the purifying step is concentrated sulfuric acid.

13. The process according to claim 1 wherein the solvent used in the purifying step is selected from the group consisting of acetone, methyl ethyl ketone, methyl isobutyl ketone, toluene and mixtures thereof.

14. The process according to claim 1 wherein the purifying step further comprises treatment with an organic solvent and water mixture.

15. The process according to claim 14 wherein the organic solvent mixed with water is acetone.

* * * * *